METHOD AND APPARATUS FOR TREATING BLOOD

Original Filed Dec. 13, 1963 8 Sheets-Sheet 1

INVENTOR.
JOHN C. ILG
BY
Dike, Thompson, Bronstein & Mrose
ATTORNEYS

METHOD AND APPARATUS FOR TREATING BLOOD

Original Filed Dec. 13, 1963 8 Sheets-Sheet 2

INVENTOR.
JOHN C. ILG
BY
Dike, Thompson, Bronstein & Mrose
ATTORNEYS

METHOD AND APPARATUS FOR TREATING BLOOD

Original Filed Dec. 13, 1963 8 Sheets-Sheet 3

INVENTOR.
JOHN C. ILG
BY
Dike, Thompson, Bronstein & Mrose
ATTORNEYS

METHOD AND APPARATUS FOR TREATING BLOOD

Original Filed Dec. 13, 1963 8 Sheets-Sheet 4

INVENTOR.
JOHN C. ILG
BY
Dike, Thompson, Bronstein & Mrose
ATTORNEYS

METHOD AND APPARATUS FOR TREATING BLOOD

Original Filed Dec. 13, 1963 8 Sheets-Sheet 5

INVENTOR.
JOHN C. ILG
BY
Dike, Thompson, Bronstein & Mrose
ATTORNEYS

METHOD AND APPARATUS FOR TREATING BLOOD
Original Filed Dec. 13, 1963 8 Sheets-Sheet 6
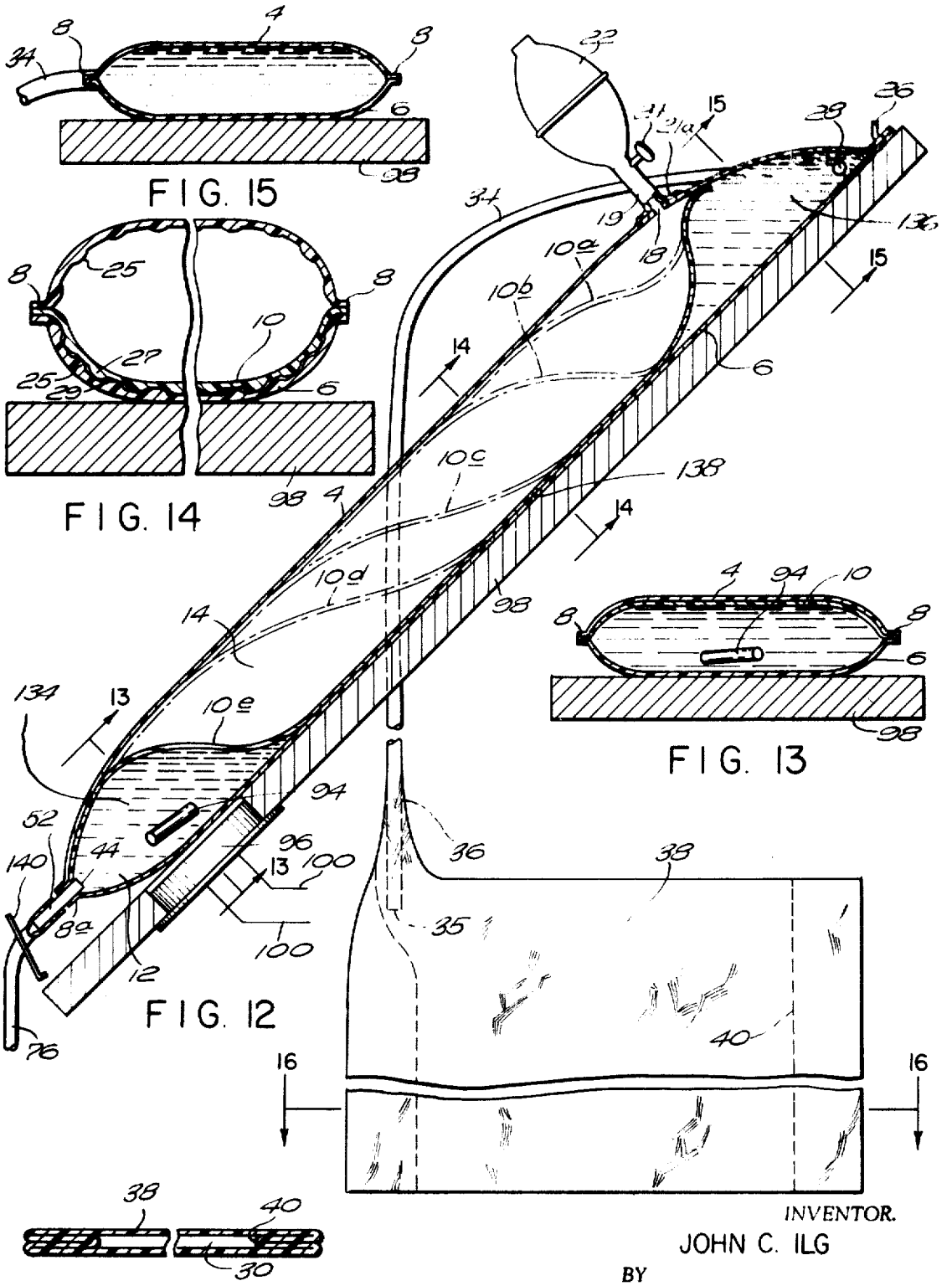
INVENTOR.
JOHN C. ILG
BY
Dike, Thompson, Bronstein & Mrose
ATTORNEYS

METHOD AND APPARATUS FOR TREATING BLOOD

Original Filed Dec. 13, 1963 8 Sheets-Sheet 7

Inventor:
John C. Ilg,
by
Dike, Thompson, Bronstein & Mrose
Attorneys

METHOD AND APPARATUS FOR TREATING BLOOD

Original Filed Dec. 13, 1963 8 Sheets-Sheet 8

Inventor:
John C. Ilg,
By Dike, Thompson, Bronstein & Mrose
Attorneys

United States Patent Office

Re. 27,359
Reissued May 9, 1972

27,359
METHOD AND APPARATUS FOR TREATING BLOOD

John Ilg, Fitzwilliam, N.H., assignor to C. R. Bard, Inc., Murray Hill, N.J.

Original No. 3,328,255, dated June 27, 1967, Ser. No. 331,342, Dec. 13, 1963, which is a continuation-in-part of Ser. No. 297,854, July 26, 1963. Application for reissue Nov. 24, 1969, Ser. No. 888,178
Int. Cl. A61k *17/00;* B01d *21/00;* C12b *1/00*
U.S. Cl. 424—101 48 Claims

Matter enclosed in heavy brackets [ ] appears in the original patent but forms no part of this reissue specification; matter printed in italics indicates the additions made by reissue.

*ABSTRACT OF THE DISCLOSURE*

*Method of washing blood cells in a closed and sterile system and in a seal flexible bag by adding a sufficient amount of a non-electrolyte washant to the blood cells in the bag to reduce the electrolyte concentration to a point at which the blood cells are precipitated to form a lower precipitated blood cell strata and an upper spent washant strata and separating the spent washant strata from the precipitated blood cell strata by flexing the bag.*

*The washing step forms part of a method for freezing blood cells for storage and thawing them, wherein the blood cells are added to the bag together with an additive to prevent cell damage by freezing, are then frozen in the bag, are then thawed in the bag and are then washed, as aforesaid, in the bag. After removal of the spent washant strata from the blood cell strata, the precipitated blood cells are resuspended and are collected in a closed and sterile manner in a flexible sterile satellite bag which is sealably secured to the wash bag.*

This application is a continuation-in-part of my application Ser. No. 297,854, filed July 26, 1963, and now abandoned.

The present invention relates to a method and disposable apparatus for washing blood cells and recovering the washed cells in a closed system. It also relates to a novel method and disposable apparatus for freezing blood cells, washing from the thawed frozen cells additives added prior to freezing to prevent cell damage and recovering the washed cells for reconstitution to whole blood all in a closed system in which the danger of contamination is reduced to a minimum.

In the past, blood banks have had to rely on refrigeration. By keeping the blood cool it has been possible to store it up to a maximum of twenty-one days. After that, by Federal Regulation, refrigerated blood must be disposed of. This not only results in a considerable waste but also means that more blood cannot be kept on hand for emergencies. Thus, for many years there has been an urgent need for some way of storing blood for long periods without spoilage.

It has been attempted in the past to fulfill this need by freezing blood. The methods and apparatus involved are elaborate and so expensive as to be impractical for civilian hospitals. One of the problems involved was that freezing of the blood damaged the blood cells. It was discovered that such damage could be prevented by adding an additive such as glycerine to the blood before freezing. However, it is essential to remove the additive from the thawed blood before it can be used. This was attempted by elaborate, expensive and bulky centrifuge equipment which is not entirely practical from a civilian hospital standpoint. One of the problems involved was to ensure against contamination during the rather extensive handling of the blood required.

It is an object of the present invention to provide a simple, inexpensive, safe and practical method and disposable apparatus for freezing blood and treating the thawed blood to make it safe for use. In this way, blood can be stored for long periods of time with no harmful effects.

It is yet another object of the present invention to provide a simple, inexpensive, safe and practical method and disposable system for removing from the frozen blood, additives added to it prior to freezing to prevent cell damage, hereinafter referred to as additives, without the necessity of complicated centrifuge. The invention is not limited however, to the removal of such additives from the blood but is also useful fo removing any other type of undesired soluble materials from the blood and also to separate red blood cells from other blood constituents without the necessity of centrifuging.

The present invention is based on the discovery that by reducing the electrolyte concentration of blood below about 0.1% (0.02 M) by the addition of a large volume of washant, such as wash water, the red blood cells are precipitated out, the additive remaining in the washant. The precipitated red blood cells and the spent washant form well defined strata, the heavier red blood cells forming the lower strata. By removing the upper spent washant strata, the red blood cells, free from additive, are left with no necessity of complicated centrifuges or other equipment. Upon addition of plasma and other blood constituents to the precipitated, washed red blood cells to form reconstituted whole blood the electrolyte concentration is increased substantially above 0.1%, i.e., to normal whole blood concentration, and the red cells become again suspended as in whole blood. The washant preferably contains a non-electrolyte, such as a sugar or an amino acid, and preferably the washing step is carried out at an acid pH, i.e. a pH below 7.0, preferably below 6.5. It is believed that the gamma globulin in the blood is instrumental in the precipitation. See Science, Feb. 8, 1963, vol. 139, No. 3554, pp. 504–505.

By removing most of the plasma by centrifuging prior to freezing and adding it to the thawed, washed red blood cells, the amount of washant required to reduce the electrolyte concentration to a concentration at which the red cells are precipitated, is reduced. Also, the washant would wash the plasma away if it was present with the red cells during washing.

The present invention provides a simple, inexpensive, safe, disposable closed system, for carrying out the above techniques with minimum risk of contamination.

In accordance with the present invention, the washing and removal of the spent washant strata from the red blood cell strata are carried out in a container or bag having a flexible wall, such removal being provided by flexing of the flexible wall to force the upper spent washant strata out of the container leaving the washed red cell strata.

More specifically, the thawed red blood cells are washed and precipitated and the spent wash water strata is removed from the red blood cell strata in a novel, inexpensive, disposable, flexible and collapsible wash bag made of a flexible, transparent or translucent plastic of the type conventionally used to make blood bags. In a preferred embodiment, the bag is elongated and has a pair of opposed outer flexible and collapsible walls and an intermediate wall dividing the bag into a gas chamber and a liquid chamber sealed from each other. By introducing gas into the gas chamber its volume is increased and the volume of the liquid chamber is decreased by flexing of the flexible intermediate wall common to both chambers, whereby the level of the stratified liquid in the liquid chamber is forced upwardly without disturbing the strata until the upper spent washant strata flows out of an outlet at the top of the liquid chamber, such flow continuing with resulting rising of the interface of the two strata until the spent washant upper strata has completely flowed out of the bag after which the gas pressure in the gas chamber is released and the washed red cells from which the additive has been removed fall back to the bottom of the bag.

The precipitation of the red cells to form such strata coupled with the extreme simplicity of the above mentioned manner of removing the upper spent wash water strata provides an extremely simple disposable and inexpensive technique for removing the additive from the red blood cells and recovering the washed cells without the necessity of centrifuge.

Preferably, the liquid chamber is longer than and extends upwardly beyond the upper end of the gas chamber, e.g. by making the intermediate wall shorter than the two outer walls, and the spent washant outlet is located at the upper end of the liquid chamber above the gas chamber.

Another feature of the invention is the provision of stirring means within the sealed liquid chamber operated by means outside the bag to achieve stirring in the closed system. The stirring means is a magnetic stirring rod rotated by a rotating magnetic field created by a mechanism outside the bag. Accordingly, it is another object of the present invention to provide a novel stirring mechanism for stirring blood (e.g. the red blood cells and washant), blood components and parenteral fluids in closed systems by means of a magnetic stirring rod inside the system and actuated by a mechanism outside the system which creates a rotating magnetic field which rotates the rod.

Preferably, the washant inlet to the liquid chamber of the bag is at the bottom of the bag although this is not essential. The washant inlet comprises flexible plastic tubing integral and disposable with the bag.

Also, in a preferred embodiment, the outlet for the spent washant at the top of the bag comprises flexible plastic tubing integrally connected at one end to the wash bag and at the other to a sealed plastic bag having very thin walls and in which the spent washant is collected whereby the washant collection bag and wash bag form a closed system disposable together.

Also, in a preferred embodiment, the washed red blood cells are reconstituted into whole blood in the wash bag by adding plasma and other blood constituents, the electrolyte in the plasma and other constituents raising the electrolyte concentration to that of whole blood and above 0.1% so that the red blood cells again become suspended. To provide for this a plasma inlet is provided, preferably at the bottom of the bag, comprising a flexible plastic tube integral and disposable with the bag and having a cannula at its end.

Also, in a preferred embodiment, the wash bag is also a freezing bag in which the blood is frozen and stored and in which the additive is added to the red cells with stirring by the magnetic stirrer referred to above. In such case, red blood cell and additive inlets are provided at the bottom of and integral with the bag. In a preferred embodiment, these inlets comprise tubing integral with the bag and having a cannula for connection with a container containing the red blood cells and a drip chamber and cannula for connection with a container containing the additive, the drip chamber being for the purpose of measuring the amount of additive. After the red cells and additive are added the tubing is tied and cut off followed by freezing of the red cells in the wash bag.

Whole blood is drawn from the donor into a blood storage container, e.g. plastic blood bag, containing anticoagulant and the red cells are separated from the plasma in the blood bag by centrifuging, the plasma being drawn off leaving the red cells. It is these red cells which are introduced into the wash and freeze bag followed by adding the additive.

In a preferred embodiment, the bottom of the blood bag, i.e. the liquid chamber, has a washed blood outlet comprising flexible plastic tubing integral with the wash bag at one end and integral with a flexible, plastic and collapsible blood bag at the other end. The washed blood outlet has a closure normally closing the outlet during addition of red blood cells and additive to the wash bag and during freezing, washing, removal of spent washant and reconstitution of the blood but which is manipulable from outside the bag to open the outlet after the blood cells are reconstituted, whereby the reconstituted blood flows into the blood bag. After the blood bag is full the tube is tied off and cut and the blood in the blood bag is ready to be administered, the blood bag having a sealed outlet for administration. The integral connection between wash bag and blood bag provides a closed system.

All of the cannulae and the outlets of the blood bag are covered and sealed by a unique type of cap and seal. The cap is made of a resilient flexible material, e.g. rubber, having an opening for receiving the cannula tip which is normally smaller in diameter than the tip so that the cap resiliently grips the tip. The open end portion of the cap and the part of the cannula adjacent thereto have a band of shrinkable plastic material shrunk tightly around them to provide a seal. Accordingly, it is another object of the invention to provide a unique but simple and inexpensive protective sealed covering for cannulae and other openings in a closed system for handling blood, blood constituents and parenteral solutions, which covering prevents against contamination but is simple to remove.

The outlet of the blood bag is provided with a novel type of closure in the form of a plug located in a piece of resilient, flexible plastic tubing sealed between the sealed peripheries of the walls of the blood bag with a portion extending out of the bag over which the aforesaid protective cap is placed. The plug is larger in diameter than the normal diameter of the tube so that it is gripped by the tube to form a seal. The plug seats on a seat (slight shoulder) in the tube located outwardly from the plug. When the cannula of a blood administration set is inserted into the tubing it forces the plug out of the tubing into the blood bag to provide communication between the cannula and bag. The diameter of the cannula is slightly larger than the tubing so that when it is inserted in the tubing the fit is a snug one. Accordingly, it is yet another object of the invention to provide a unique but simple closure for outlets of plastic blood bags, which closure is manipulable from outside the bag and outlet to open the closure.

Preferably, the wash bag and associated tubing and blood bag are made of a transparent plastic which can be easily packaged in a relatively small compact package.

Other objects and advantages will be apparent from the following description and the accompanying drawings which describe and show for illustrative purposes only an embodiment of the invention and in which drawings.

Figure 1:
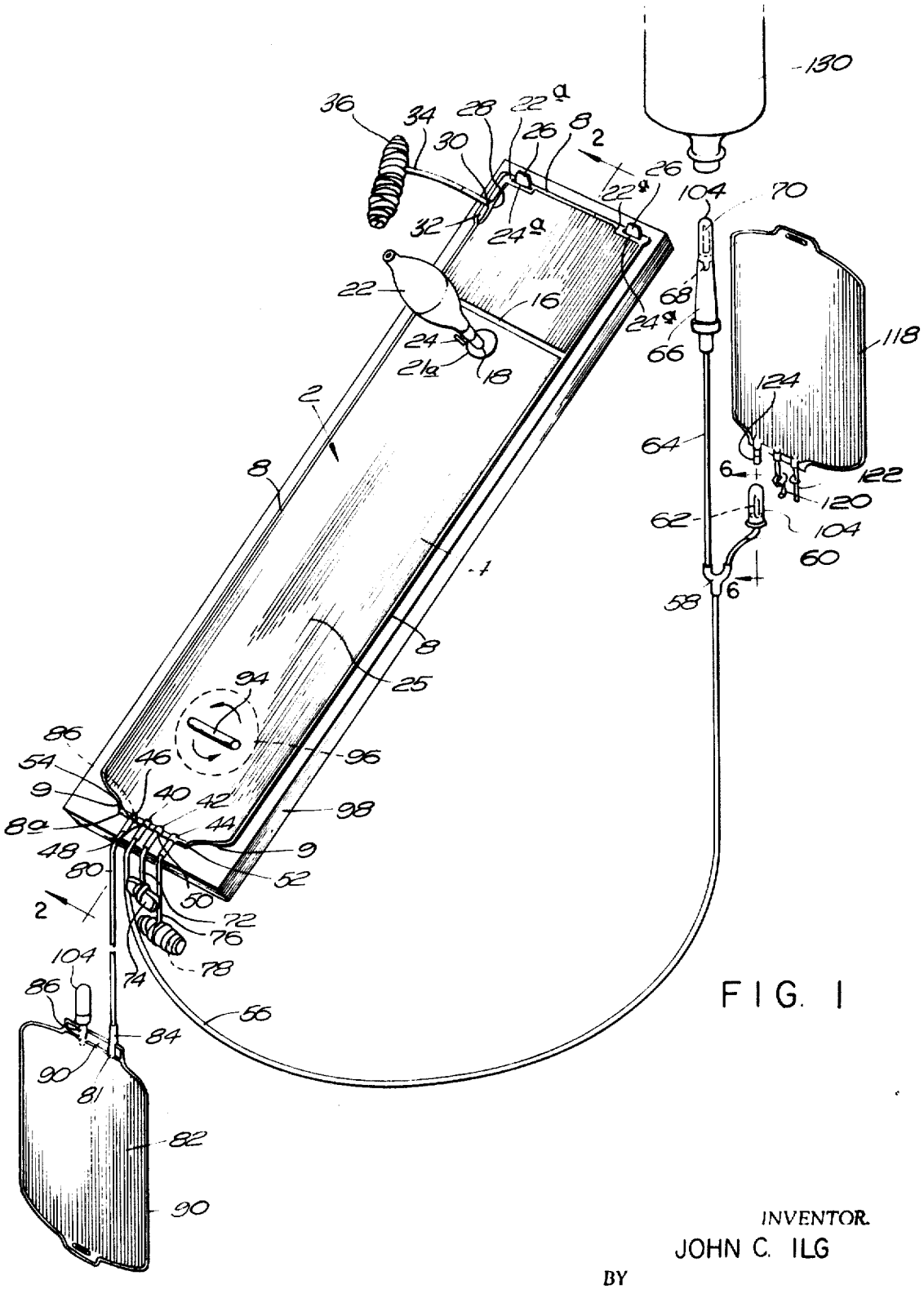
FIG. 1 is a view in perspective of an embodiment of the present invention.
Figures 2, 3, 4, 6:
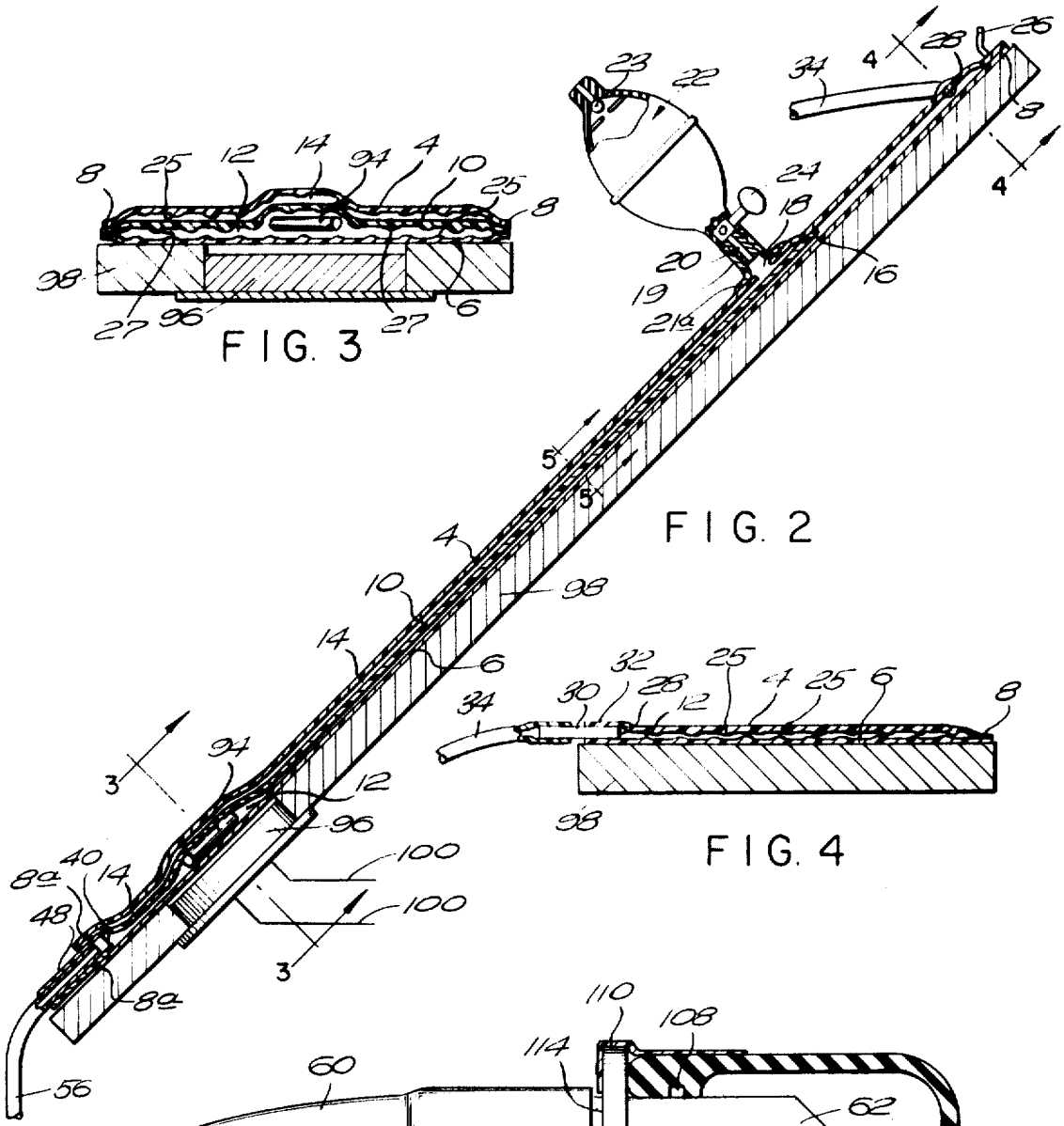
FIG. 2 is a vertical section taken along the line 2—2 of FIG. 1.
FIG. 3 is a horizontal section taken along the line 3—3 of FIG. 2.
FIG. 4 is a horizontal section taken along the line 4—4 of FIG. 2.
FIG. 6 is a section taken along the line 6—6 of FIG. 1.
Figure 9:
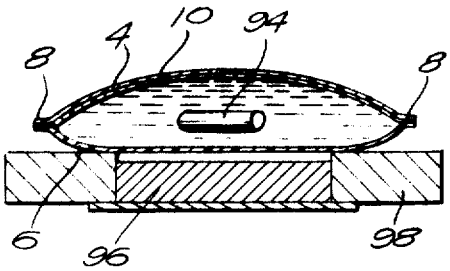
Figure 8:
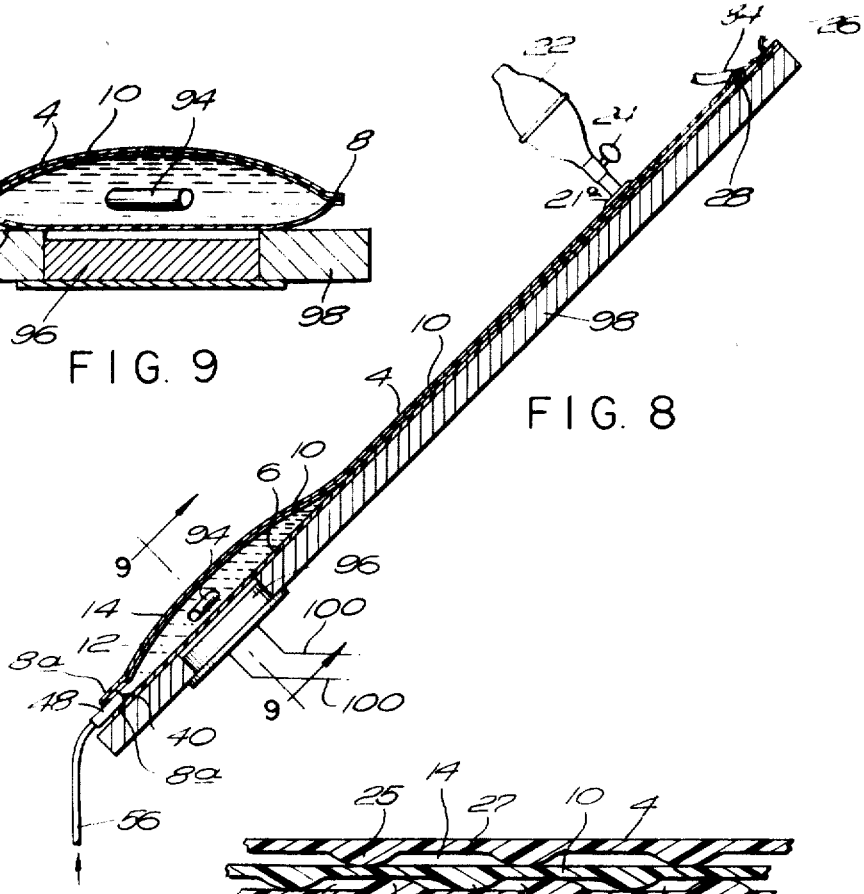
FIG. 8 is a vertical section like FIG. 2 but after the red blood cells and additive have been added before freezing.
Figure 10:
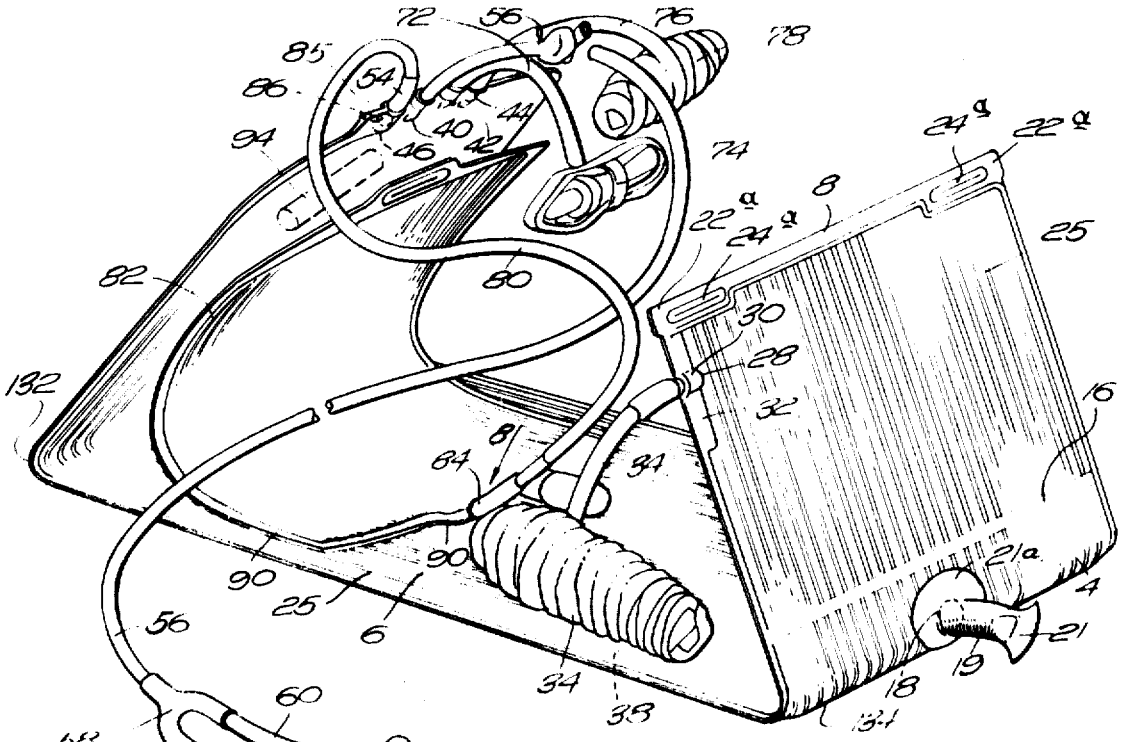
Figure 17:
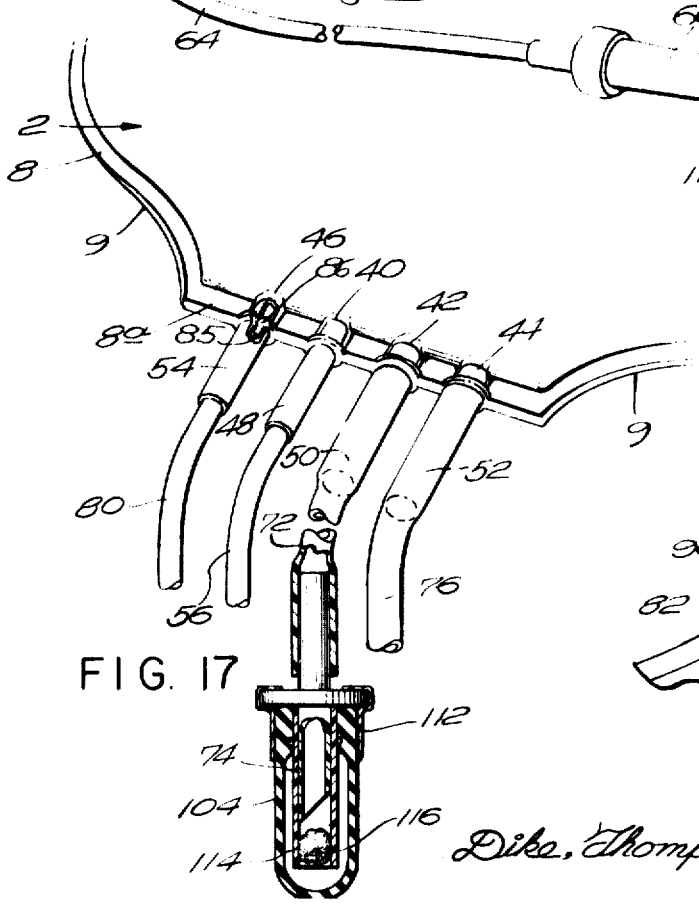
Figure 18:
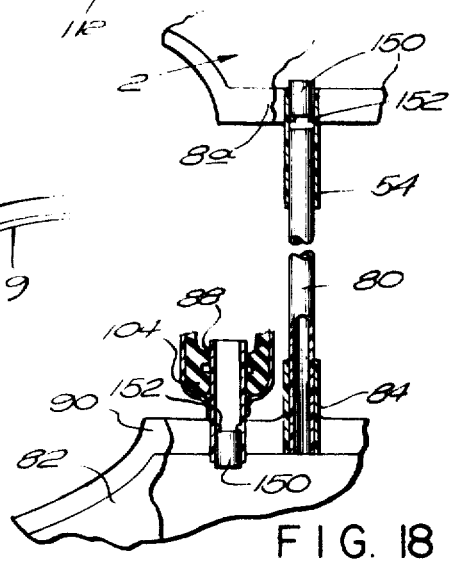
Figure 11:
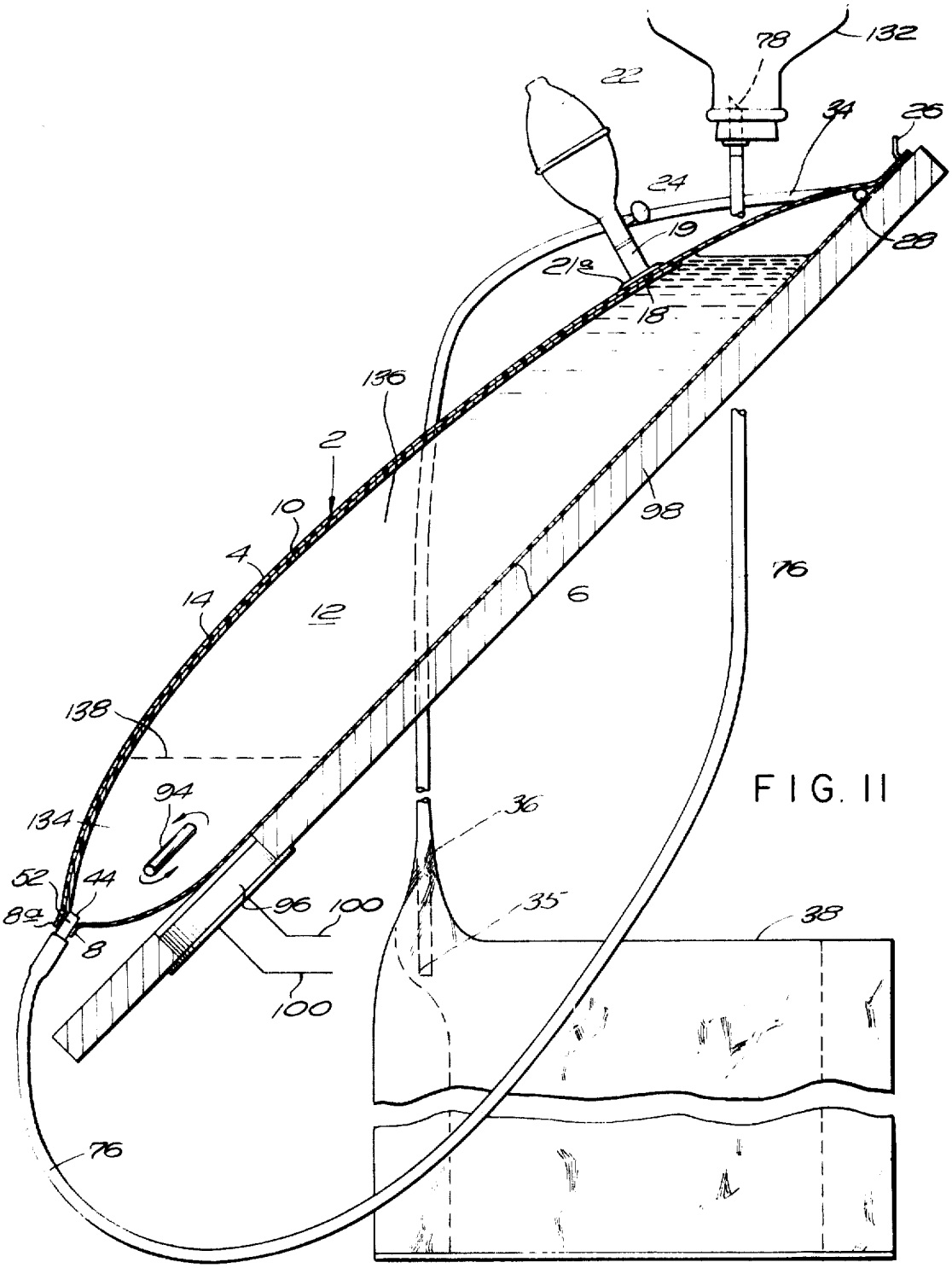

FIP. 9 is a horizontal section taken along the line 9—9 of FIG. 8 with the parallel longitudinal ribs on the walls of the wash bag omitted for simplification;

FIG. 10 is a view in perspective of the wash bag showing how it is folded for storage and freezing after the red blood cells and additive are added and after the inlet tubing for inletting such cells and additive is tied and cut off, the cut off tubing also being shown in the figure;

FIG. 11 is a view like FIG. 2 showing the bag with the washant added to the unthawed blood cells and additive with stirring by the magnetic stirrer to precipitate the red blood cells and wash out the additive, the interface between the red blood cell strata and spent washant strata after cessation of stirring being shown in broken lines;

FIG. 12 is a view like FIG. 2 showing the various stages of expansion of the gas chamber and contraction of the liquid chamber to force the upper spent washant strata containing the extracted additive out of the top of the wash bag, leaving the precipitated, washed red blood cells in the bag, the final stage of expansion being shown in full lines and the intermediate stages in broken lines;

FIG. 13 is a view taken along the line 13—13 of FIG. 12 with the parallel longitudinal ribs on the walls of the wash bag omitted for simplification;

FIG. 14 is a view taken along the line 14—14 of FIG. 12;

FIG. 15 is a view taken along the line 15—15 of FIG. 12 with the parallel longitudinal ribs on the walls of the wash bag omitted for simplification;

FIG. 16 is a view taken along the line 16—16 of FIG. 12;

FIG. 17 is an enlargement of the bottom part of the wash bag of FIG. 1;

FIG. 18 shows the use of a plug other than a ball for the reconstituted blood outlet from the wash bag and the outlet from the blood bag.

Figure 19:
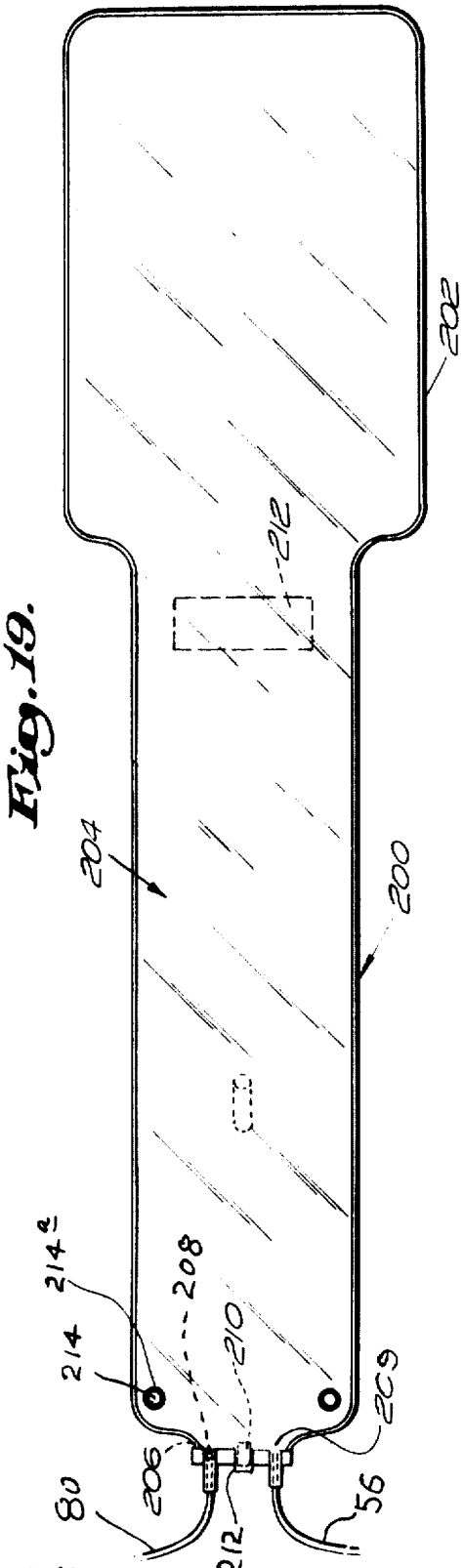
Figure 20:
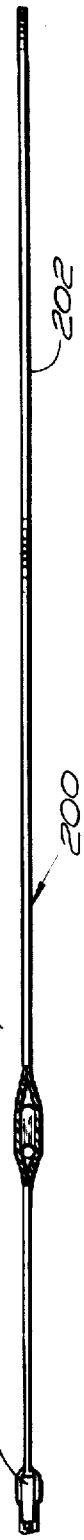
Figure 21:
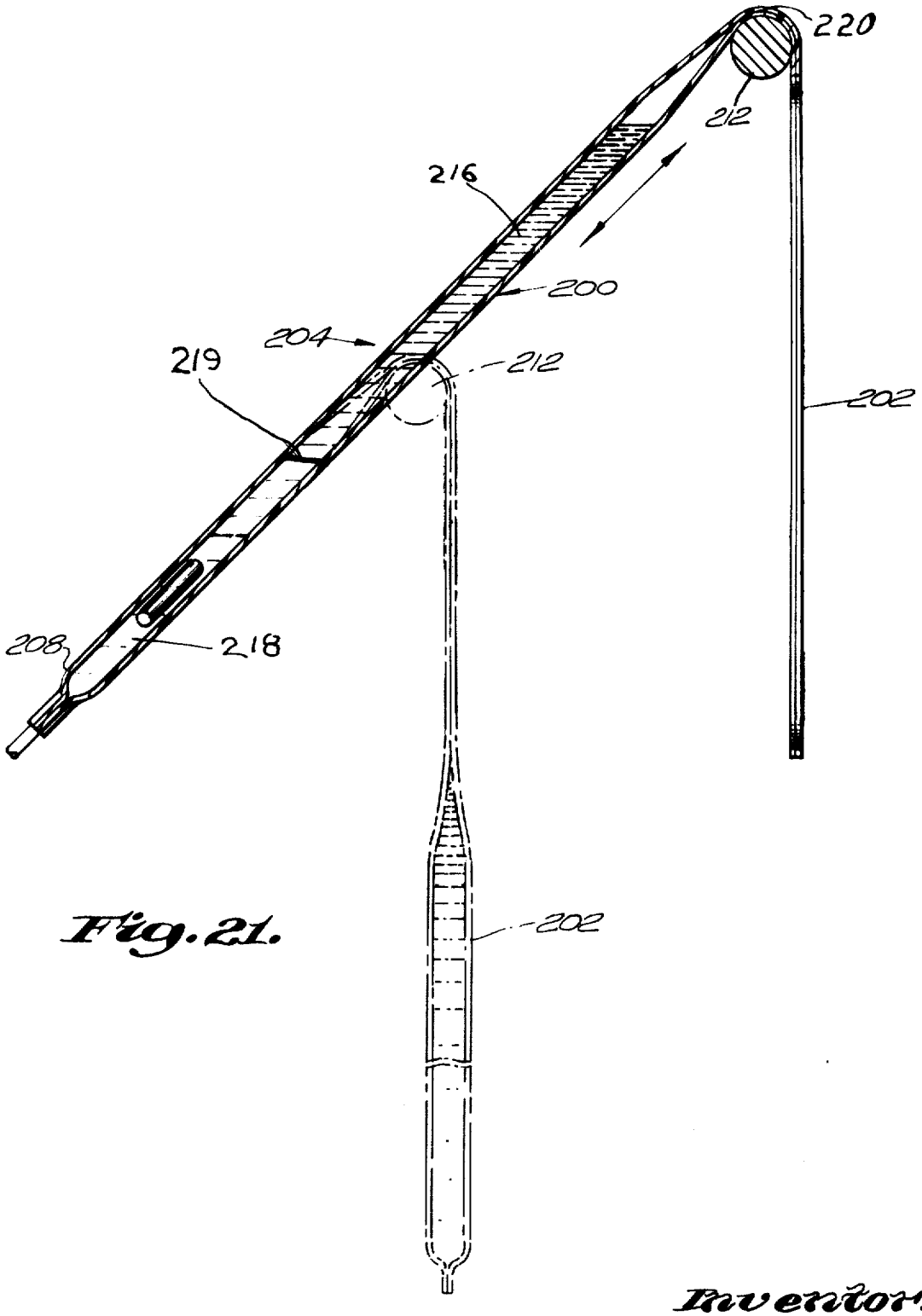

FIG. 19 is a view of another embodiment of the wash bag of the present invention;

FIG. 20 is a side view partially in section of the bag of FIG. 19;

FIG. 21 is a view showing another way of separating the spent washant strata from the precipitated blood cell starta in the blood bag of FIG. 19, the position of the parts after stratification but before separation being shown in full lines and the position of the parts during separation being shown in broken lines.

With reference to the figures, 2 represents a flexible walled, collapsible and disposable wash bag embodying the present invention. The walls of the bag and its associated tubing are made of a flexible, tough, transparent or translucent plastic of the type used in conventional plastic disposable blood bags, such as polyvinyl chloride resins, e.g. polyvinyl chloride acetate copolymers trichlorofluoroethylene, polyethylene, etc. which can withstand sterilization conditions (gas or autoclaving), which are chemically inert, hemorepellant, nonreactive, impermeable and non-wettable, which have a glossy surface such as delays the coagulation and degradation of blood and which can withstand the extremes of heat and cold in storage including freezing conditions for long periods of time. The relatively thin wall sizes employed for the tubing and bag are flexible and elastic, i.e. self restoring. The thin wall thicknesses of the bags are flexible and collapsible so that they are capable of lying flat.

The bag is elongated, as shown, and comprises a pair of opposed flexible, transparent outer walls 4 and 6, which are sealed together along their outer peripheries at 8, and an intermediate, flexible, transparent plastic inner wall 10 which divides the bag into a liquid chamber 12 and an air or gas chamber 14. Intermediate wall 10 is of the same width but is not as long as the two outer walls 4 and 6. It is sealed along its lower and side edges to the lower side edges of the two outer walls at 8. However, its upper edge does not extend to the upper edge of the two outer walls and such upper edge is sealed to the outer wall 4 along the seam 16 but not to outer wall 6. Thus, the liquid chamber 12 and air chamber 14 are sealed from each other and the liquid chamber is longer than, and extends upwardly beyond, the gas or air chamber.

The portion of seam 8 at the lower edge of the bag is slightly wider at 8a than the rest of the seam 8.

The gas chamber is formed by the lower part of outer wall 4 and intermediate wall 10 and the liquid chamber is formed by outer wall 6, intermediate wall 10 and the portion of outer wall 4 above the sealed seam 16.

The air chamber 14 has an air inlet 18 which extends into a short length of tubing 19 which is sealed to the wall 4 by flange 21a and which is adapted to receive the metal shank 20 (FIG. 2) of a conventional flexible rubber pressure bulb assembly 22 by which air can be pumped into the air chamber 14 to expand it. The pressure bulb assembly has a conventional valve 24 which is shut when air is pumped into the air chamber by squeezing the bulb. By opening the valve 24, the air pressure in the air chamber is released. The pressure bulb is also provided in a conventional manner with a one way valve 23 which is closed when the bulb is squeezed so that the air in the bulb is forced into chamber 14, and opened when the squeezing force is released so that the air in the bulb is replenished. Pressure bulb assembly 22 is of the conventional type used in equipment for measuring blood pressure.

In the wash bag 2, as manufactured and sold, the end of tube 19 is sealed at 21 (FIG. 10) and remains sealed during freezing and storage. When the thawed blood is to be washed the sealed end 21 of the tube is cut off by a scissors or knife and the shank 20 of the pressure bulb assembly is attached, as shown, by insertion into the open end of tube 19.

Figure 5:
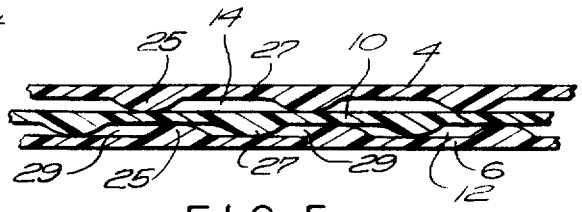
FIG. 5 is an enlarged view of part of a horizontal section taken along the line 5—5 of FIG. 2 to show the parallel longitudinal ribs on the walls of the wash bag.

The inner surfaces of outer walls 4 and 6 are provided with parallel, longitudinally extending ribs 25 (see FIG. 5). The surface of intermediate wall 10 facing wall 6 is also provided with such parallel, longitudinally extending ribs 27. The ribs extend along the entire length of the walls and are evenly spaced along the entire width thereof. The ribs 25 are staggered with respect to the ribs 27 and provide longitudinally extending passages 29 between the outer wall 6 and intermediate wall 10 when the two walls are forced together, as described in detail hereinafter. The ribs 25 of each of the outer walls 4 and 6 are also staggered with respect to each other.

The sealed seam 8 at the top of the bag is slightly wider at its ends 22a. Horizontal slits 24a are provided in those widened portions 22a for supporting or hanging the bag on hooks 26.

The upper portion of the liquid chamber 12 is provided with an outlet 28 for outletting spent washant as described hereinafter. Outlet 28 extends through a widened upper portion 32 of a sealed side edge 8 of the bag and is located close to the top of the liquid chamber 12 well above the seam 16. Outlet 28 comprises a short piece of plastic, transparent tubing 30 extending through the upper widened portion 32 of the sealed side edge 8, such upper portion 32 being slightly wider than the rest of the sealed seam 8, as aforesaid. The sealed side edge portions 32 of the outer walls 4 and 6 are sealed around and to the periphery of tubing 30, as shown. The outer end of the tubing 30, which outer end extends outwardly beyond the side edge of the bag, is sealed by cement or otherwise (FIGS. 1 and 4) within the end of a long length of larger diameter, transparent plastic tubing 34, the other end 35 (FIGS. 11 and 12) of which is received within an opening 36 in the top of a disposable spent washant collection bag 38 made of very thin, flexible, transparent plastic like that used for garment bags, e.g. polyethylene. The portion of the bag 38 around the opening 36 is gathered and wrapped around the end 35 of tube 34 and is sealed thereto so that wash bag 2, tubing 34 and bag 38 form a closed system with the end 35 of the tubing extending into the bag 38, as shown. Bag 38 is otherwise sealed at its edges and the side portions thereof are provided with expansion folds 40 (FIG. 16) so as to reduce the dimension of the unfilled bag. When the bag 38 is filled the folds expand to increase the capacity of the bag. The wash bag assembly is packaged and the blood is introduced into, and frozen in, the wash bag 2 with the spent washant collection bag 38 rolled up tightly and with the length of tubing 34 wrapped tightly around the rolled bag 38 as shown in FIGS. 1 and 10. An elastic band is placed around the rolled bag 38 and tube 34 to prevent them from unrolling. They are unrolled just prior to contracting the liquid chamber to expel the spent washant strata through tube 34 and into the bag 38. They are shown unrolled in FIGS. 11 and 12. The thinness of the material of bag 38 permits it to be rolled into a small package while at the same time having a sufficient capacity to hold a large total volume of washant used, for example, when the red blood cells are washed a number of times. When the bag 38 and tube 34 are rolled as shown in FIG. 1, the rolled tubing is flattened to thereby close the tubing and prevent the flow of liquid from the wash bag 2 into the bag 38 and most of the tubing 34.

The lower end of the liquid chamber 12 of the wash bag is provided with a red blood cell and additive inlet 40 for inletting the red blood cells and additive prior to freezing, a plasma inlet 42 for inletting plasma and other blood constituents to reconstitute the washed thawed red blood cells after freezing, a washant inlet 44 for inletting washant to precipitate the thawed red cells and wash the additive out of the thawed cells, and a reconstituted blood outlet 45 for outletting the reconstituted, washed and thawed blood. In each case the outlet or inlet comprises a short length of flexible plastic transparent tubing 48, 50, 52 and 54 respectively, extending through the lower sealed edge 8a of the wash bag 2 between the sealed lower edge portions 8a of the outer wall 6 and intermediate wall 10, such lower edge portions being sealed around and to the outside of the short-lengths of tubing. These lengths of tubing protrude downwardly a short distance beyond the lower edge of the bag 2 for attachment to larger lengths of plastic tubing as described hereinafter. The lengths of tubing 50 and 52 are slightly larger in diameter than 48 and 54.

It is noted that the lower side edges 8 of bag 2 are tapered inwardly at 9 to the lower edge 8a of the bag.

Sealed within the protruding portion of tubing 48 (the red blood cell and additive inlet) is the end of a relatively long length (116 I.D.) of flexible, transparent, plastic tubing 56 (FIGS. 1 and 2) which branches at 58 into a red blood cell branch 60, having a cannula 62 sealed thereto at its end, and an additive branch 64 having a transparent drip chamber 66 sealed thereto at its end, the drip tube 68 of which drip chamber extends upwardly into cannula 70. Tubing 56 is of smaller diameter than tubing 48 so that the end thereof is receivable within the protruding end of tubing 48, as shown.

The protruding end of tubing 50 (plasma inlet) is sealed within the end of a length of larger diameter flexible, transparent plastic tubing 72 (.234 I.D.), the other end of which tubing 72 is provided with a cannula 74 sealed thereto. The bag 2 is packaged with the tubing 72 rolled tightly around the longitudinal length of the cannula 74 and tubing 72, as shown in FIGS. 1 and 10, remains so rolled during addition of the red cells and additive to the wash bag and during freezing, washing and removal of the spent washant. This arrangement prevents the escape of liquid from the bag through this tubing because rolling the tubing around the cannula in this manner pinches it together to thereby block the passage of liquid. The tubing is unrolled, as shown in FIG. 17, just prior to the introduction of plasma into the bag.

The protruding end of tubing 52 (wash solution inlet) is sealed in an end of a relatively long length of larger diameter (.234 I.D.) flexible, transparent plastic tubing 76, the other end of which is provided with a cannula 78 sealed thereto (see FIGS. 1 and 11). The wash bag 2 is packaged with the tubing 76 wrapped or rolled tightly around the longitudinal length of the cannula 78 and such tubing remains so rolled when the red cells and additive are added to bag 2 and during freezing. This arrangement prevents the escape of liquid from the bag through tubing 76 since rolling the tubing in this manner pinches the tubing shut. The tubing 76 is unrolled when it is desired to add washant to the bag, as shown in FIG. 11.

Sealed within the protruding end of tubing 54 (outlet for reconstituted blood) is the end of a smaller diameter flexible, transparent, plastic tubing 80, the other end of which is sealed within the inlet 81 of a flexible, transparent, plastic blood bag 82 comprising two opposed flexible transparent plastic walls sealed along their peripheral edges at 90, the above mentioned inlet 81 to the blood bag comprising a short length of plastic tubing 84 extending through and sealed in a sealed edge 90 of the bag 82 and protruding outwardly from such edge, as shown in FIGS. 1 and 10. The end of tubing 80 is sealed in tubing 84 so that the wash bag 2, blood bag 82 and tubing 80 form a closed system.

Within the portion of outlet tubing 54 located in the seam 8a is a hard plastic ball 86 (FIGS. 1, 10 and 17) which functions as a closure normally shutting off communication between wash bag 2 and blood bag 82. Ball 86 is larger in diameter than the normal diameter of the flexible and resilient tubing 54 so that it is gripped tightly by the tubing to form a seal preventing passage of fluid from wash bag 2 to blood bag 82. Ball 86 seats on a seat 85 (FIGS. 10 and 17) in tubing 54 to prevent the ball from moving outwardly too far. The ball can be forced out of the tubing 54 into bag 2 by manipulation of tubing 54 from outside the bag and tubing to thereby provide communication between wash bag 2 and blood bag 82. The ball normally closes such communication during addition of the red cells and additive to the wash bag and during freezing, washing, removal of the spent washant and addition of the plasma to reconstitute the blood cells. Thereafter, it is manipulated out of tubing 54 into the wash bag 2 to transfer the reconstituted blood to the blood bag 82.

Blood bag 82 has an outlet 86 (FIGS. 1 and 7) comprising a short length of flexible, transparent, plastic tubing 88 extending through a sealed edge 90 of the blood bag, the sealed edges of the walls of the bag being sealed around and to the tubing 88. Tubing 88 extends slightly into the blood bag and also protrudes outwardly of the sealed edge 90 as shown. A ball 92 is located in tubing 88, as shown, and functions as a closure normally closing tubing 88 and hence outlet 86. The diameter of the ball 92 is larger than the normal diameter of the flexible, resilient tubing 88 so that the ball is gripped tightly by the tube to form a seal therebetween. The horizontal diameter of the ball is located slightly below the seal strip 90, i.e., it is located within the portion of tubing 88 protruding into the bag. The ball seats against a seat 94 within tubing 88 to prevent it from being forced outwardly out of the tubing. As aforesaid, normally ball 92 seals the tube 88. However, when it is desired to administer the reconstituted blood from the blood bag 82, movement of the cannula of the blood administration set into the tubing 88 forces the ball 92 out of the tubing 88 into the bag 82 so that communication is provided between the cannula and blood bag interior. The normal diameter of the tubing 88 is smaller than that of the cannula so that the tubing grips the cannula to ensure against leakage.

Located within the liquid chamber 12 of wash bag 2 is a magnetic stirring rod 94 which is rotated end over end about an axis perpendicular to the longitudinal axis of the rod 94 and perpendicular to the plane of the bag 2 from outside the bag 2 by a rotating magnetic field which is created by a rotating magnetic field creating device 96 of conventional design.

The stirrer is operated during addition of the red blood cells and additive to mix them thoroughly and during the washing operation to mix the washant with the red cells and additive. During these operations and also during removal of the spent washant strata by contracting the liquid chamber, as will be described hereinafter, the bag is supported on a board 98 at an inclination to horizontal, e.g. at an inclination of about 45° to horizontal, by means of a pair of hooks 26 on the board 98 and the slits 24a. This aids in preventing stirring rod 94 from falling to the bottom of the bag. However, the rotating magnetic field also holds the rod 94 from falling to the bottom of the bag during operation. The inclination of the bag may vary widely.

The rotating magnetic field creating device 96 is located in a recess in board 98 and is provided with electrical leads 100.

This magnetic stirring device permits stirring in the closed system.

Figure 7:
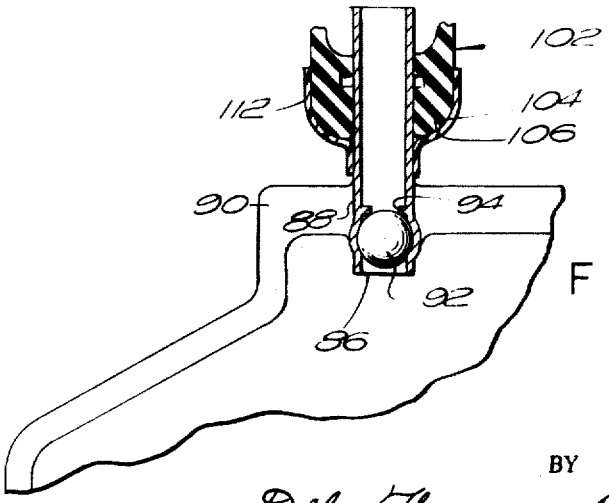
FIG. 7 is an enlarged view in vertical section showing the outlet of the blood bag for collection of the thawed, washed and reconstituted blood from the wash bag.

All of the cannulae and the tubing 88 forming the outlet 86 of the blood bag 82 are provided with a unique protective covering 102 (FIGS. 6 and 7) to protect against contamination. The covering comprises a resilient, flexible rubber cap 104 placed over the cannula tip 62, as shown in FIG. 6, and over the protruding portion of tubing 88, as shown in FIG. 7, and having a reduced diameter portion 106 at its open end which receives the cannula tip 62. The reduced diameter 106 is normally less than the diameter of the cannula tip 62 so that the portion 106 resiliently grips the cannula tip to form a seal. The bore of the reduced diameter portion 106 has an annular groove 108 therein closer to the inner end of the reduced portion than the outer end, as shown, to provide a better seal. The portion of 106 inwardly of the groove 108 is slightly smaller in diameter than the portion of 106 outwardly of the groove 108 for better gripping and sealing. The cap 104 is moved over the cannula tip 62 until the open end engages the cannula flange 110 as shown. A thin annular band 112 of a shrinkable plastic such as cellulose resin, sold by Du Pont de Nemours under the trade name Cell-O-Seal, is shrunk tightly around the open end portion 106 of the cap 104 and the flange 110, as shown, to provide an excellent seal and to hold the cap on the cannula. Shrinkage of the plastic band 112 around portion 106 of the rubber cap squeezes such portion tightly against the outer periphery of the cannula tip to incerase the sealing effect. Shrinkage of the band 112 around the flange 110 causes the end portion of the band to move against the flange surface 114, as shown, to hold the cap 104 firmly on the cannula. These cellulose bands, having an inside diameter sufficient to be placed over the cap and cannula, are purchased wet and after being placed in the proper position over the cap and cannula they are dried. Drying shrinks them tightly around the cap and cannula as shown. However, heat shrinkable plastics can be used also. In the case of the tubing 88 of blood bag 82 (FIG. 7), the band 112 is shrunk around portion 106 of the cap and a part of tubing 88, as shown. In the case of the cannula 70 at the end of the drip chamber 66, the band 112 is shrunk around portion 106 of the cap 104 and the upper portion of the drip chamber adjacent the cannula. In all cases the cap is held firmly over the cannula and tubing 88 by the band 112 but it can be removed by pulling it off or by breaking the band 112.

The tip of cannula 74 (plasma inlet) has a flexible, plastic sleeve 114 (see FIG. 17) located over it with a light friction fit and extending outwardly beyond the pointed end of the cannula 74, the outer end of the sleeve 114 having a plug of cotton 116 therein. Sleeve 114 is received with the cannula tip 74 within the protective cap 104 and is pulled off the cannula tip with the cap. The purpose of the sleeve 114 and cotton plug 116 is for gas sterilization of the unit. That is, after the entire unit has been assembled with all the protective caps in place except for the cap for the plasma inlet cannula 74 and with sleeve 114 and cotton plug 116 in place, the entire unit is gas sterilized, the sterilizing gas entering the interior of the unit through the cotton plug in the sleeve. After sterilization the sterilized cap 104 for the plasma cannula 74 is placed over the cannula and sleeve 114. The sleeve 114 protects the cannula tip from contact with the cap or the hands which might not be sterile. Since the sleeve comes off with the cap, the cap never touches the cannula tip.

The entire system is a closed one, the only openings being the plasma, washant, red blood cell and additive cannulae inlets but these are protected by the protective caps 104 and bands 112 until ready for use.

The entire apparatus is disposable and with it the additive can be added to the red cells and the red cells frozen, thawed, washed free of additive, reconstituted and transferred to the blood bag in which it is ready for use all in a safe, disposable, inexpensive, closed system with minimum danger of contamination.

The bag assembly is packaged as shown in FIG. 10 except that the tubing 56 and its branches, cannulae and protective coverings for the cannulae are not cut off, as in FIG. 10, but are intact as per FIG. 1, the rolled tubing 34, 72, and 76, as well as the tube 56 and its branches, being folded in the wash bag 2 and the wash bag, as shown in FIG. 10, being again folded in the middle to provide a compact unit which is packaged in a plastic bag (not shown) which holds it in its folded condition.

The method of using the above apparatus will now be described.

First the blood is taken from the donor in a conventional plastic blood bag 118 (FIG. 1) containing an anticoagulant in a conventional manner through the tubing 120 after which the tubing is tied and cut. Thereafter, the red blood cells are separated from the plasma by centrifuging in bag 118 in conventional manner, the plasma being removed from the bag through the plastic tubing 122, leaving the red cells and some white cells unless they too are separated out by centrifuging. After plasma removal tubing 122 is tied and cut as shown. The amount of red cells left in bag 118 may be about 300 cc. of which about 80% is packed red (and white) blood cells and 20% is plasma, the plasma having an electrolyte (e.g. sodium chloride) concentration equivalents to about 0.85% NaCl.

Thereafter, the wash bag unit is removed from the plastic bag (not shown) in which it is packaged and is placed on board 98 at an angle of about 45°, the wash bag being supported by hooks 26, as shown. The stirrer 94 is manipulated from outside the bag a substantial distance above the bottom of the wash bag as shown.

Thereafter, cap 104 is removed from the cannula 62 (FIG. 1) and the conventional protective cap (not shown) over the outlet 124 of blood bag 118 is also removed. Cannula 62 is then inserted in the outlet 124 through a conventional pierceable sealing diaphragm therein to provide communication between the cannula and the interior of the blood bag. The outlet 124 may be provided with a plug which is forced out of the outlet 124 into the blood bag by insertion of the cannula. The blood bag 118 is elevated above the bottom of the wash bag, as shown, to permit the red cells to flow from the blood bag into the liquid chamber 12 of wash bag 2 through tube 60, 56 and inlet 40. At the same time, the magnetic stirrer 94 is actuated by energizing the leads 100, e.g. by a switch, so that the blood cells are stirred as they flow into the bag.

Thereafter, the cap 104 of cannula 70 is removed and the cannula inserted in a hole in the sterilized stopper of a sterilized bottle 130 of the additive, after which the bottle is inverted above the wash bag to permit a measured flow of additive through the drip chamber 65, branch 64, tubing 56 and inlet 40 into the liquid chamber 12 of the bag 2 while the stirrer 94 is operated, whereby the additive is thoroughly mixed with the red blood cells. The wash bag with the red cells and additive added is shown in FIG. 8.

A preferred additive is dimethyl sulfoxide in the form of an 8.6 molar solution in a 6% glucose-1% fructose aqueous solution, about 300 cc. of such solution being added to and admixed with the red cells.

The purpose of the additive is to prevent damage to the red blood cells during the freezing and thrawing steps.

The purpose of the glucose and fructose is to equalize the concentration of solute inside and outside the blood cells when the additive is added to the cells. Without the glucose and/or fructose or some other non-electrolyte, upon addition of the additive the solute concentration outside the cells would be much less than that inside the cells and the resulting migration of water from inside the cell to outside the cell by osmosis caused by the difference in solute concentration might cause cell rupture.

The addition of the additive reduces the electrolyte concentration of the resulting mix to about 0.17% at which the red blood cells remain suspended in the water and plasma.

After the additive has been added the tubing 56 is tied tightly close to the bag and then is cut, as shown in FIG. 10.

The bag 2 is then removed from board 98 and laid flat so that the contents are spread out in the bag after which the bag is folded as shown in FIG. 10 with the rolled tubing folded within the bag, as shown. The folds 132 and 134 when the bag is folded flat form seals so that the blood cells remain distributed throughout the liquid chamber.

The unit is then placed in a freezer and the blood cells frozen. They can remain frozen for long periods of time.

When it is desired to use the blood cells the unit is removed from the freezer and the blood cells permitted to thaw. Thereafter, the bag is placed on board 98, as shown, at an angle of about 45° and the stirrer 94 manipulated from outside the bag a short distance, about a fourth or less of the bag length, above the bottom of the bag. Then the tubing 76 is unrolled or unwrapped from around its cannula 78, and 104 removed from cannula 78 and the cannula inserted into the sterilized stopper of a sterilized bottle 132 (FIG. 11) of washant preferably comprising a 6% aqueous solution of dextrose and 1% fructose. The stirrer 94 is then actuated and the bottle 132 is raised above the wash bag 2, as shown, so that the wash water flows through tubing 76 and inlet 44 into the liquid chamber 12 of bag 2 where it is thoroughly admixed with the red blood cells and additive by the stirrer 94. About 1500 to 2000 cc. of wash water are added with stirring. Stirring is continued until thoroughl mixing is achieved. It is usually best to stir the thawed cells and additive a short time before addition of the wash water. FIG. 11 shows the bag after the wash water has been added.

Because of the large volume of wash water, which contains no electrolyte, the electrolyte concentration in the liquid chamber is reduced below about 0.1% (0.02 M) and consequently the red blood cells are precipitated out leaving the additive in the wash water. The blood cells are thoroughly washed by the wash water to remove the additive and also some or all of the residual plasma, which remain in the wash water.

When stirring is discontinued, the precipitated washed red blood cells collect at the bottom of the wash bag with the spent wash water, containing the removed additive and plasma, at the top of the bag above the red blood cells. The cells and spent wash water form well defined strata 134 and 136 respectively with an interface 138, as shown in FIG. 11.

Thereafter, the spent wash water collection bag 38 and tubing 34 are unrolled as in FIG. 12 and a clamp 140 is applied to the tubing 76 close to the wash bag to shut off the tubing 76.

Then the sealed end 21 of the air tubing 19 is cut off by a scissors and the pressure bulb 22 connected to such tubing as shown. Air is then pumped into the air chamber 14 by continuously squeezing and releasing the pressure bulb to expand the air chamber 14 and reduce the volume of the liquid chamber 12, as shown in FIG. 12, the expansion of chamber 14 commencing at the top of the air chamber at the air inlet and working down from 10a to 10e to increasingly reduce the volume of the liquid chamber. The air pressure in the air chamber 14 forces the intermediate wall 10 toward the oposite outer wall 6, as shown in FIG. 12.

Expansion of the air chamber expands the intermediate wall 10 against the opposite outer wall 6, as shown in FIG. 12, the area of contact between wall 10 and wall 6 working down and increasing as the air pressure is increased in the air chamber. The ribs 25 and 27 form channels 29 (FIG. 14) between the two walls 10 and 6 at the area of contact therebetween to permit the flow of liquid upwardly from below the contact area to above the contact area.

As the air chamber 14 is increased in volume and the liquid chamber is correspondingly decreased in volume the upper wash water strata is forced or squeezed upwardly in the liquid chamber out of outlet 28 and tube 34 into collection bag 38 without destroying or disturbing the well defined blood cell and spent wash water strata. Since all the other inlets and outlets to and from bag 2 are closed, the liquid in chamber 12 has no place else to go.

As the liquid chamber volume continues to be decreased and more of the upper spent wash water strata is squeezed or forced out of the top of the liquid chamber, the interface 138 rises until it is located in the passages 29 with the lower precipitated red blood cell strata 134 below the contact area and the spent wash water strata 136 above the contact area, position 10e of the flexible intermediate wall 10 in FIG. 12. Thereafter, the flow of the spent wash water out of the liquid chamber continues by siphon action, the interface 138 continuing to rise, until all of the spent wash water strata is removed and red blood cells commence to flow out of outlet 28. The operator can observe this because of the transparency of the wash bag and the tube 34 and at this point he releases the pressure in the pressure chamber 14 by opening valve 24 of the pressure bulb, i.e. after all the spent wash water phase has flowed out of the wash bag but before any substantial amount of red blood cells flow out of the bag. Upon release of the air pressure, the air chamber contracts i.e. the flexible walls thereof collapse, and the washed red cells fall back to the bottom of the liquid chamber. At this stage the wash bag appears as shown in FIG. 8. The lower end 35 of the tube 34 should be below the level of the wash bag to ensure the above mentioned siphon action. Also, preferably no part of tube 34 should be above outlet 28. Otherwise, it is necessary for the red cells to pass the highest point of the tube 34 in order to insure against wash water in the upper part of the tubing falling back into the bag when the pressure is released in the air chamber.

Preferably, this washant removal step is followed by at least two other identical washing and removal steps, i.e. the clamp 140 is released and another 1000 or 1500 or 2000 cc. of wash water is admitted to the wash bag through tubing 76 with stirring followed by another wash water removal step. After the last washing step the red cells at the bottom of the wash bag are free from additive.

Thereafter, the tubing 34 and 76 are tied tightly in a knot close to the bag and are cut, the plasma tubing 72 is unrolled and the protective cap 104 and sleeve 114 removed from the cannula 74 at the end thereof and the cannula is inserted into the sterilized outlet of a sterilized bag or bottle (not shown) of plasma and other blood constituents to be added to the red cells to reconstitute them into whole blood. The magnetic stirrer is actuated and the bottle or bag of plasma is raised above the wash bag to cause plasma to flow through tube 72 into the liquid chamber where it is thoroughly admixed with the red cells by the stirrer. The addition of the plasma (which contains about 0.85% electrolyte) increases the electrolyte concentration in the liquid chamber of the bag above 0.1% so that the red blood cells again become suspended in the plasma and other blood liquids as in whole blood. After addition of the plasma, the plasma tube 72 is tied and cut close to the bag.

Thereafter, the ball 86 is manipulated by the fingers from outside the system, out of the tubing 54 of the outlet 46 into the liquid chamber of wash bag 2. This is achieved by manipulating the tubing 54 to force the ball out of the inner end thereof into the wash bag. Upon forcing the ball out of the tubing the reconstituted blood flows into the blood bag 82 through tube 80. Thereafter tubing 80 is tied in a knot and cut off close to the bag 82 and the reconstituted blood in bag 82 is ready to be administered. The rest of the unit can be thrown away.

The blood in bag 82 is administered by removing the protective cap 104 from the tubing 88 (FIG. 7) and inserting the cannula of the blood administration set into tubing 88. The cannula forces the ball 92 out of the tubing 88 into the blood bag and the blood flows through the cannula and other parts of the administration set to the patient.

In the particular embodiment shown in the drawings the wash bag is about 19½ inches long and about 5½ inches wide and the sealed seam 16 is about 5 inches below the top of the bag. However, these dimensions are not critical.

The particular volume of red cells and additive and wash water added to the wash bag are not critical. It is enough to say that an amount of additive is added sufficient to prevent red cell damage during freezing and thawing and an amount of wash water is added sufficient to reduce the electrolyte concentration in the liquid chamber to a concentration at which the red cells will precipitate, i.e below about 0.1%, and to wash the additive out of the red cells. A lesser volume of wash water can be used per wash step with a greater number of wash steps.

The wash water contains the non-electrolyte glucose and/or fructose for the same reason as the additive, namely to make the concentration of solute outside the red cells after addition of the wash water about the same as it is inside the cells to thereby prevent rapid migration of water through the cell walls from inside the cells to outside the cells by osmosis at a rate which is apt to cause damage to (bursting of) the cell walls. Without the non-electrolyte, the addition of the large volume of wash water to the cells will result in a very low solute concentration outside the cells as compared to inside the cells with resulting rapid migration of water through the cell walls from inside the cells to outside the cells (water flows through a membrane from a more concentrated to a less concentrated solution), which might result in bursting of the cell walls. The greater the difference in concentration the more rapid the flow of water through the cell walls. The amount of electrolyte in the wash water need not be such as to make the soluble concentration outside the cells exactly the same as that inside the cells so long as it is enough to reduce the difference in concentrations inside and outside the cells to an amount which will prevent cell damage. The amount may range from slightly hypotonic (about 200 milliosmols per kilogram) to about two and one half times normal osmotic strength, or approximately 750 milliosmols per kilogram.

In place of glucose and/or fructose in the additive and wash water, any suitable non-electrolyte can be used such as dextrose, sucrose and other types of sugars as well as amino acids such as glycine. It is obvious that an electrolyte cannot be used since one of the functions of the wash water is to reduce the electrolyte content in the bag so as to precipitate the red cells.

The plasma is removed from the red cells prior to freezing for two reasons, (1) if the plasma was not removed too much wash water would be required to lower the electrolyte concentration sufficiently to precipitate the red blood cells and (2) the plasma would be washed away with the wash water.

If desired, the removed plasma can be frozen separately but with the red cells and added to the cells after they have been thawed and washed or other plasma can be added to the thawed, washed cells. Plasma can be kept for relatively long times, even without freezing. Preferably, if the plasma of the donor is used it is treated to remove any danger of hepatitis.

During washing, some of the white cells are removed with the washant. This is an advantage and the white cells removed are manufactured rapidly by the body of the recipient of the blood. As a matter of fact, the present apparatus and method can be used to separate red cells from white cells. This is achieved by washing the red and white cells as described a number of times whereby the red cells are precipitated out and the white cells are removed with the wash water from which they can be recovered by other means if desired.

Although dimethyl sulfoxide is the preferred additive to prevent cell damage during freezing and thawing, others can be used such as glycerine, ethylene glycol and other glycols and glycerols.

The pH during the washing step should preferably be acidic, i.e. below 7.0, preferably below about 6.5, to achieve good precipitation. Above about pH 6.1, i.e. between about 6.1 and 6.5, settling of the precipitated or clumped or agglomerated red cells is somewhat retarded. The pH optimum for settling is between about 5.2 and 6.1. Human red blood cells in ACD anticoagulant (acid citrate dextrose), which is the standard anticoagulant, fortunately fall within this optimum pH range. Consequently no pH control is normally necessary. Since the washant does not contain any electrolyte it does not affect the pH.

A preferred magnetic stirrer is one sold under the trade name Magmix by Precision Scientific Corporation. The iron stirring rod is coated with Teflon. This manner of stirring by a magnetic stirrer actuated by a rotating field created outside the bag is an important feature of the invention. To my knowledge, it has never been used before in handling blood or parenteral fluids. It is useful not only in the wash bag shown and described but can also be used in conventional disposable and non-disposable blood bags such as 118 and bags for handling parenteral fluids where mixing is desired in a sealed or closed system without rendering the blood or other fluid unsterile. Such use comes within the present invention. For example, in conventional plastic blood bags, the bag in which the blood is collected contains an anticoagulant. By use of the magnetic stirrer of the present invention, good mixing of the anticoagulant and blood is achieved. In any case where such stirrer is used, it is advantageous to hold the bag at an inclination to vertical during stirring as shown in the drawings.

The stirring rod in operation should be held a sufficient distance above the bottom of the bag so that it can turn freely without hitting the bottom and so that it creates an even swirling of the fluid.

Although the wash bag and method described and shown is used for freezing, washing and reconstituting the blood cells, it can be used to wash the blood cells without freezing. For example, the thawed frozen blood cells containing the additive and frozen in another container can be introduced into the wash bag and washed as set forth above. Furthermore, the red cells can be removed from the wash bag before being reconstituted in which case the plasma inlet can be eliminated. Also it is not necessary to have the blood bag 82 integrally connected with the wash bag, in which case the blood outlet would comprise merely tubing with a cannula at the end. In fact the reconstituted blood can be administered directly from the wash bag.

Also, if desired, the washant inlet tubing and/or the additive branch 64 can be integrally connected with a supply of sterilized washant or additive, e.g. a sealed plastic bag full of washant or additive and having a ball closure at its outlet which can be manipulated out of the outlet to provide flow to the wash bag.

Not only can the wash bag be used for washing frozen red blood cells to remove the additive but also to wash any blood cells, frozen or not, to remove any undesired constituents and to isolate the blood cells. For example, it can be used as aforesaid to separate the white cells from the red cells. By precipitation of the red cells they can be isolated from other normal blood constituents or from any kind of additive or undesirable material which is not a normal blood constituent.

Although the walls of the bag shown have ribs, grooves can be provided.

The liquid chamber is made longer than the gas chamber and the spent wash water outlet is located above the upper end of the gas chamber to insure against the outlet being closed by the expanding intermediate wall 10.

It is preferred that the air inlet to the gas or air chamber be located at the upper end of the chamber so that expansion thereof and contact of the wall 10 with the wall 6 works downwardly as air pressure is increased.

The use of the three wall construction, two other walls and an intermediate wall, can be used for blood bags for collecting and storing blood of the type shown as 118. In such case the intermediate wall may be of the same size as the outer walls, i.e., extend across the width and length of the bag to provide a liquid and air chamber, the liquid chamber having either conventional inlet and outlet constructions as in bag 118 or an outlet of the type shown in FIGS. 7 and 18.

Although the use of a ball 86 and 92 has been shown and described for closing the outlet 46 of the wash bag and the outlet 86 of the blood bag 82, a cylindrical shaped solid plug 150 (FIG. 18) made for example of Teflon or Kel F or other compatible material can be used, which is plugged tightly into the inner end of the tubing 54 in the case of the wash bag and tubing 88 in the case of bag 82. The diameter of the plug is larger than the normal diameter of the tubing into which it is pluged so that it is gripped tightly by the tubing to form an excellent seal. In the case of the wash bag, the plug can be forced out of the tubing 54 into the wash bag by manipulation of the tubing from outside the system and in the case of the blood bag 82 the plug is forced into the blood bag by insertion of the cannula of the blood administration set into the tubing 88. A slight seat 152 is provided as in the case of the ball to prevent movement of the plug in the wrong direction. The advantage of such a plug over a ball is that it provides an annular contact and sealing area between its periphery and the inside of the tubing rather than a circular sealing line of contact to thereby provide a better seal. Also, in the case of the blood bag the cannula strikes the flat bottom of the plug to force it out of its tubing. With a ball, the point of the cannula is apt to be wedged between the ball and tubing which interferes with movement of the ball out of the tubing. The plug may be tapered slightly at one end to facilitate plugging into the tubing.

Although in the embodiment shown in the drawings, the wash bag is made from flat panels sealed along their peripheries, it can be made from a length of flattened plastic tubing of the proper inner diameter to give the bag dimension desired, and sealed at its ends. A third wall may be sealed to the outside of the flattened tubing to form the gas chamber. Also, smaller diameter tubing may be sealed within larger diameter tubing, the annular space between the tubing forming the gas chamber.

Although the use of a three-wall, flexible plastic bag provides an excellent way of carrying out the step of removing the spent plasma strata from the wash bag in the method of the present invention, a two wall plastic flexible bag can be used, e.g., the wash bag shown and described without the intermediate wall 10, in which case the upper washant strata is removed by applying a controlled compressive force to the outside of the bag to compress the bag and squeeze the washant strata out of the bag without disturbing the stratified condition of the two strata. However, this requires great care and control in applying the compressing force not only to prevent mixing of the two strata but also to prevent loss of red cells due to over-compression, and is quite difficult to do correctly by hand.

Such a bag and method are shown in FIGS. 19 to 21 in which transparent, flexible, plastic bag 200 is made like that of FIG. 1 except that the shorter intermediate wall is omitted and the upper end thereof has a widened extension portion at 202, the lower narrower elongated part 204 being about the same length (between 19 and 26 inches but preferably 25 or 26 inches) and width (between 5 and 7 inches but preferably 6 or 7 inches) as the entire bag of FIG. 1. The widened extension portion 202 may be between about 10 and 11 inches wide and about fifteen inches long and takes the place of the spent washant outlet 28, tube 34 and bag 38 of the FIG. 1 embodiment in that it functions as a spent washant collection bag, as will be described more fully hereinafter. The lower end of the bag has only three ports, one being the balled outlet 206 corresponding to 46 in FIG. 1 communicating with the blood collection bag 82 through tubing 80 as in the FIG. 1 embodiment and containing a ball valve 208 like ball 86 of the FIG. 1 embodiment. Another of the three ports is a blood cell and additive inlet 209 corresponding to 40 in FIG. 1 and communicating with tubing 56 and cannulae 62 and 70 attached thereto exactly like the FIG. 1 embodiment for inflow of blood cells and additive. The third port is formed by a short length of plastic tubing 212 sealed into the lower sealed seam of the bag and having a cylindrical nylon seal plug 210 fitted tightly in the opening at the inner end thereof to seal the port, such tubing and plug having the construction shown in FIG. 18.

The protruding end portion of the tubing 212 has a protective covering (not shown) exactly like 102 (with cap 104) shown in FIG. 18.

The washant is added to the bag through a separate feed tubing (not shown) having a cannula at an end thereof which is inserted into the tubing 212 (after removal of protective covering 102) to force the plug 210 into the bag (the cannula is gripped tightly by the tubing 212 to form a seal) whereby the feed tubing is placed in communication with the interior of the bag. The plasma and other materials added to reconstitute the blood are added through the same feed tubing after completion of washing, such materials being added to the feed tubing through a branch having a cannula at the end thereof with a protective covering like 102. This branch may also be provided with a flexible plastic drip chamber or other measuring device. The washant is added through another pair of branches beyond the plasma adding branch, such washant being flowed simultaneously from two bottles or containers through the two branches into the feed tubing. The ends of the two branches are provided with cannulae with protective coverings like 102 and the internal diameters of the two branches are greater than that of the rest of the feed tubing. Clamps are provided to close off the feed tubing from the bag during strata separation, to close off the washant branches during addition of the plasma through the plasma branch to reconstitute the blood and to close off the plasma branch when the washant is being added through the washant branches.

The upper end of the bag has no openings in it.

The inner surfaces of the bags have longitudinal ribs as in the FIG. 1 embodiment.

The lower narrow elongated portion 204 of the bag has a capacity of at least 1200 cc. and preferably 2500 cc. to 3000 cc. but it may be as large as 4000 cc. or 5000 cc. whereas the enlarged end 202 has a capacity of from 4000 or 5000 cc. to 10,000 cc. or more. In a preferred embodiment the capacity of 202 is about 9000 cc. The capacity of enlarged portion 202 should be at least twice, and preferably three times, that of the narrow portion 204.

Washing of the blood cells is carried out in the lower narrow portion of the bag while it is supported in an inclined position, as shown in FIG. 2, the upper part of the narrow portion being folded over a steel support roller 212, as shown, with the wide portion 202 hanging downwardly on the side of the roller opposite the inclined narrower portion. Most of the narrow portion of the bag in which washing is done lies on the other side of the roller at an incline, as shown. The opposed walls of the bag along the top of the supporting roller are squeezed into contact with each other by the roller due to the weight of the bag. The holes 214 at the bottom of the bag are located in small circular seal area 214a where the walls are sealed together, and are adapted to receive pins for holding the bottom of the bag on the support, as shown.

After washing the blood cells in the narrow inclined portion of the bag, as already described, the top spent washant strata 216 is separated from the bottom precipitated blood cell strata 218 (interface shown as 219) by moving the roll downwardly relative to the bag in the direction shown by the arrow in FIG. 21 to move the squeeze area 220 downwardly and thereby decrease the size of the liquid chamber between the roller 212 (the squeeze area 220) and the bottom of the bag. As the squeeze area is moved downwardly to decrease the size of such chamber, the spent washant is forced past the squeeze area (over and past the roller) and then falls downwardly by force of gravity into the enlarged portion 202 of the bag on the other side of the roller. The ribs on the inner bag surfaces permit flow of the liquid past the squeeze area. Also the roll 212 is not as wide as the narrow portion 204 of the bag at the squeeze area so the liquid can flow in the bag along the sides of the squeeze area past the roller. Because of the nature of the bag (the walls thereof are normally flat and collapsed against each other) and the ribs, once the liquid starts to flow upwardly past the squeeze area and then downwardly into the enlarged end of the bag, a siphon action occurs. The roller is continued to be moved downwardly to thereby move the squeeze area toward the lower bag end until substantially all of the upper spent washant strata is removed after which it must be moved upwardly rapidly to break the siphon action. The roll may be mounted on screw jacks on a frame to provide the above mentioned movement, such screw jacks preferably being driven by means of an electric motor.

It is apparent that the action is the same as the FIG. 1 embodiment except that instead of applying a squeezing force and moving the squeeze area downwardly toward the lower bag end to decrease the size of the liquid chamber between such squeeze area and the bottom of the bag and thereby force the spent washant upper strata to move upwardly past the squeeze area, by means of pneumatic pressure (air chamber), as in FIG. 1, it is done mechanically by means of roller 212. In both, the liquid emerging from the squeeze area is removed from such area by flowing it downwardly by gravity. In both, there is a siphon action. However, instead of an additional washant collection bag 38 located below the squeeze area so that spent washant emerging from the squeeze area will flow downwardly away from the squeeze area through a tube 34 between such collection bag and the blood bag, the upper part of the blood bag is made bigger and by folding the bag over the roller, such upper portion is located below the squeeze area and acts as a collection bag.

The capacity of the enlarged part of the bag should be at least two times, and preferably three times that of the narrow portion so that it can hold the washants from at least two, and preferably three, washings, the roller 212 being returned to its full line position after each separation followed by the succeeding wash and then by separation of the spent washant strata from the blood cell strata as aforesaid.

The height of the narrow, blood washing bag portion in all embodiments should preferably be at least two, and preferably, three times its width in order to provide proper control during stparation of the strata.

The three-wall bag permits the required carefully controlled and incremental compression of the liquid chamber, to minimize mixing of the strata and loss of red cells due to do over-compression. The use of the roll 212 also provides such controlled and incremental compression.

Although in the preferred embodiment of the method of the present invention the spent washant strata is removed from the red cell strata by use of a container for the stratified liquid column having a flexible wall which is flexed to apply pressure to the stratified liquid column to force the washant strata out of the container, pressure may be applied to the stratified column of liquid to force the spent washant strata out of the container in which the stratified column is located by means other than a flexible wall of the container.

Instead of integrally attaching long lengths of tubing to the short tubing lengths extending through the edges of the bag, as shown in the drawings, such short tubing lengths can be provided with cannula pierceable sealing membranes or with sealing plugs, the various liquids being inletted and outletted by inserting cannulae at the ends of such long lengths of tubing through such membranes or against such plugs to force them into the wash bag.

Human blood, which has been frozen, thawed, washed and reconstituted in accordance with the method described above and in the above described apparatus, has been successfully administered to a number of patients with no harmful effects.

It will be understood that the present invention is not limited to the particular embodiments thereof illustrated and described herein and I set forth its scope in the following claims.

I claim:

1. A method of washing blood cells in a closed system comprising washing at a pH below about 7.0 said cells in a bag having at least one flexible wall with a sufficient volume of a substantially non-electrolyte washant to reduce the electrolyte concentration to a concentration at which the blood cells are precipitated to form a precipitated blood cell strata and a spent washant strata and separating the spent washant strata from the precipitated red cell strata by flexing said wall.

2. A method according to claim 1, said washant comprising a non-electrolyte aqueous solution, said volume of washant being sufficient to reduce the electrolyte concentration to below about 0.1%.

3. A method according to claim 2, said method comprising a method of removing unwanted constituents from said blood cells, said wash water washing said constituents from said blood cells, said blood cells being precipitated leaving the unwanted constituents in the spent washant.

4. A method according to claim 3, said bag being elongated and having a pair of opposed flexible and collapsible walls and a flexible and collapsible intermediate wall forming with one of said opposed walls a sealed gas chamber and with the other opposed wall a liquid chamber in which said blood cells are washed.

5. A method according to claim 4, one of said intermediate wall and said one opposed wall being shorter than the other, the end of the shorter wall being sealed to an intermediate portion of the longer to form an end of said gas chamber and to provide a gas chamber which is shorter than the liquid chamber, said longer wall extending beyond said gas chamber and being sealed at its end to the corresponding end of said other opposed wall, which is also longer than said shorter wall, to form an end of said liquid chamber, said liquid and gas chambers being sealed from each other; said liquid chamber having an outlet for said spent washant, said outlet being located at said end portion of said liquid chamber beyond said end of said gas chamber and being spaced from said end of said gas chamber toward said end of said liquid chamber.

6. A method according to claim 1, comprising introducing said blood cells into a washing chamber in said bag; adding said washant to said blood cells with stirring, terminating said stirring whereby the blood cells stratify at the bottom of said washing chamber and the spent washant forms a strata on top of said blood cells, flexing said flexible wall by applying a flexing force thereto to reduce the size of said washing chamber and thereby force the spent washant strata out of said chamber leaving the washed blood cell strata in the washing chamber.

7. A method according to claim 6, said stirring being carried out by a magnetic stirring rod within said bag, said rod being actuated from outside the bag by a rotating magnetic field, thereby permitting efficient stirring in the bag.

8. A method according to claim 6, said spent washant being forced into a flexible storage chamber integrally connected with said washing chamber to form a closed system.

9. A method according to claim 6, comprising adding to the washed blood cells in said bag, a whole blood constituent electrolyte to raise the electrolyte concentration to a concentration at which the blood cells become resuspended.

10. A method according to claim 9, comprising flowing the resuspended blood in said wash bag into a blood bag integrally attached to said wash bag in a closed system by tubing, tying said tubing connecting said blood bag and wash bag, followed by cutting said tubing.

11. A method according to claim 6 for removing an additive from thawed frozen blood cells, said additive having been added to said cells prior to freezing to prevent damage to said cells during freezing and thawing, said wash water washing said additive from said blood cells by precipitating said blood cells leaving said additive in the spent washant.

12. A method according to claim 11 forming a part of a method for freezing blood, comprising adding said blood cells and said additive to said wash bag with stirring, freezing the blood cells and additive in said wash bag, thawing the blood cells in said wash bag and thereafter performing said washing and washant separation steps.

13. A method according to claim 12, said blood cells being obtained by removing plasma from whole blood taken from a donor, leaving the blood cells for freezing.

14. A method according to claim 12, comprising adding said washant to said thawed cells and additive with stirring while said bag is inclined at an angle to vertical.

15. A method of washing blood cells in a closed system comprising washing at a pH below about 7.0 said cells with a sufficient volume of a substantially non-electrolyte washant to reduce the electrolyte concentration to a concentration at which said blood cells are precipitated to form a stratified liquid column comprising a precipitated blood cell strata and a spent washant strata, removing the spent washant strata from the blood cell strata in a container for said column by applying pressure to said stratified column to thereby force the spent washant strata out of said container without substantial intermixing of the strata, thereby leaving the precipitated, washed blood cell strata in the container.

16. A method according to claim 1, said bag being elongated and having a pair of opposed flexible and collapsible walls, at least one of which has a plurality of longitudinally extending ribs on its inner surface.

17. A method of washing blood cells in a closed system comprising washing at a pH below about 7.0 said cells in a container having at least one flexible wall with a sufficient volume of a substantially non-electrolyte washant to precipitate said blood cells to form a precipitated blood cell strata and a spent washant strata and separating the spent washant strata from the precipitated blood cell strata by squeezing said flexible wall toward an opposite wall of the said container, the squeeze area being moved toward an end of said container to decrease the size of the chamber between said end of said container and said squeeze area to force the liquid in said chamber to flow from such chamber past said squeeze area in a direction reverse to the direction of movement of the squeeze area.

18. A method according to claim 17, said flexible wall at said squeeze area being squeezed into contact with said opposite wall, said contact area being moved toward said end of the bag, said liquid being forced to flow past said contact area through at least one passage formed between said walls adjacent the contact area.

19. A method according to claim 17, said end of said bag being the lower end, said spent washant strata being the upper strata and said squeeze area being moved downwardly.

20. A method according to claim 18, said passage being formed by a plurality of longitudinally extending ribs on the inner surface of at least one of said walls.

21. A method according to claim 14, said additive being added to said cells with stirring and while said bag is inclined at an angle to vertical.

22. A method according to claim 6, said blood cells being obtained by removing plasma from whole blood taken from a donor.

23. A method according to claim 7, comprising adding said washant to said cells while said bag is inclined at angle to vertical.

24. A method according to claim 6, and said bag being a collapsible flexible, sterile, pyrogen free plastic bag through which the bag contents are visible, said spent washant being forced into a flexible storage chamber integrally connected with said washing chamber to form a closed system, adding to the washed blood cells in said bag a whole blood constituent electrolyte to raise the electrolyte concentration to a concentration at which the blood cells become resuspended, said stirring being carried out by a magnetic stirring rod within said bag, said rod being actuated from outside the bag by a rotating magnetic field, thereby permitting efficient stirring in the closed system bag, said blood cells being obtained by removing plasma from whole blood.

25. A method according to claim 24, the size of said liquid chamber being reduced from top to bottom by said flexing of said flexible wall of said bag.

26. A method according to claim 1, said bag being a collapsible flexible, pyrogen free plastic bag through which the bag contents are visible.

27. A method according to claim 18, said bag being an elongated collapsible, flexible, pyrogen free plastic bag through which the bag contents are visible.

28. A method according to claim 6, the size of said liquid chamber being reduced in a direction from top to bottom by said flexing of said flexible wall.

29. A method according to claim 7, the size of said liquid chamber being reduced in a direction from top to bottom by said flexing of said flexible wall.

30. A method according to claim 8, the size of said liquid chamber being reduced in a direction from top to bottom by said flexing of said flexible wall.

31. A method according to claim 9, the size of said liquid chamber being reduced in a direction from top to bottom by said flexing of said flexible wall.

32. A method according to claim 10, the size of said liquid chamber being reduced from top to bottom by said flexing of said flexible wall.

33. A method according to claim 11, the size of said liquid chamber being reduced from top to bottom by said flexing of said flexible wall.

34. A method according to claim 12, the size of said liquid chamber being reduced from top to bottom by said flexing of said flexible wall.

35. A method according to claim 1, said method forming a part of a method of freezing blood comprising adding said blood cells and an additive to said wash bag, freezing the blood cells in said wash bag, thawing the cells in said wash bag, thereafter performing said washing and washant separation steps in said wash bag and thereafter resuspending said cells in said wash bag, said additive being added to prevent damage to said cells during freezing and thawing.

36. A method according to claim 1, said washing step being carried out in a washing chamber in said bag, said spent washant being forced into a flexible storage chamber integrally connected with said washing chamber to form a closed system.

*37. A method of washing blood cells in a closed system comprising washing at a pH below about 7.0 said cells in a bag having at least one flexible wall with a sufficient volume of a substantially non-electrolyte washant to reduce the electrolyte concentration to a concentration at which the blood cells are precipitated to form a precipitated blood cell strata and a spent washant strata and separating the spent washant strata from the precipitated red cell strata by flexing said wall, said method forming part of a method of freezing blood comprising adding said blood cells from which plasma has been removed and an additive to said wash bag in a closed and sterile system, freezing the blood cells in said sealed wash bag, thawing the cells in said sealed wash bag, thereafter performing said washing and separation steps in a closed and sterile system, said additive being added to prevent damage to said cells during freezing and thawing, said bag being a sealed, sterile, collapsible, flexible plastic bag through which the contents thereof are visible.*

*38. A method according to claim 37 including separating the spent washant strata from the precipitated blood cell strata by removing the spent washant strata from the blood cell strate in a closed and sterile system and removing the washed blood cell strata from said bag in a closed and sterile system through a washed blood cell outlet into a disposable, sealed, collapsible, flexible, sterile, plastic washed blood cell collection bag.*

*39. A method according to claim 37, said spent washant strata being removed from said blood cell strata in a closed and sterile system through a spent washant outlet into a disposible, sealed, collapsible, flexible, plastic spent washant collection bag.*

*40. A method according to claim 39, said spent washant collection bag being sealably connected to said spent washant outlet to provide a closed sterile system between said wash bag and said spent washant collection bag.*

*41. A method according to claim 38, said spent washant strata being removed from said blood cell strata in a closed and sterile system through a spent washant outlet into a disposable, sealed, collapsible, flexible, plastic spent washant collection bag, said washed blood cell outlet being located at the lower end of said bag, said spent washant outlet being spaced a substantial distance longitudinally along said bag upwardly from said washed blood cell outlet.*

*42. A method according to claim 38, said washed blood cell collection bag being sealably connected in a closed and sterile system to said wash bag.*

*43. A method according to claim 40, said washed blood cell collection bag being integrally and sealably connected in a closed and sterile system to said wash bag.*

*44. A method according to claim 37, said sealed wash bag containing a stirrer operated from outside said bag by a rotating magnetic field during said washing step to mix the washant and blood cells.*

*45. A method according to claim 44, said stirrer being operated to mix said additive and said concentrated blood cells in said sealed wash bag prior to freezing.*

*46. A method according to claim 37, said washing step being repeated with fresh washant.*

*47. A method according to claim 37, including resuspending in a closed and sterile system said washed blood cells while in said bag and after said spent washant has been separated therefrom.*

*48. A method according to claim 37, said bag being more than two times longer than it is wide.*

References Cited

The following references, cited by the Examiner, are of record in the patented file of this patent or the original patent.

Haynes et al.: J.A.M.A., vol. 173, No. 15, pp. 1657–1663, Aug. 13, 1960.

Huggins: Science, vol. 139, No. 3554, pp. 504–505, Feb. 8, 1963.

SAM ROSEN, Primary Examiner

U.S. Cl. X.R.

195—1.8, 210—42

UNITED STATES PATENT OFFICE
CERTIFICATE OF CORRECTION

Patent No. Re27,359 Dated May 9, 1972

Inventor(s) John Ilg

It is certified that error appears in the above-identified patent and that said Letters Patent are hereby corrected as shown below:

In the specification:

Column 7, line 32 should read:

--outlet 46 for outletting the reconstituted, washed and--

Column 10, line 74 should read:

--ured flow of additive from the drip chamber 66, branch--

Signed and sealed this 5th day of September 1972.

(SEAL)
Attest:

EDWARD M.FLETCHER,JR.
Attesting Officer

ROBERT GOTTSCHALK
Commissioner of Patents